United States Patent
McGilloway et al.

(10) Patent No.: US 10,524,965 B2
(45) Date of Patent: Jan. 7, 2020

(54) FULLY PADDED DISPOSABLE DIAPER

(71) Applicants: Michelle Goldie Peters McGilloway, Piedmont, CA (US); Rebecca Julie Triki, Oakland, CA (US); Bailey Jeanne Peters, Oakland, CA (US)

(72) Inventors: Michelle Goldie Peters McGilloway, Piedmont, CA (US); Rebecca Julie Triki, Oakland, CA (US); Bailey Jeanne Peters, Oakland, CA (US)

( * ) Notice: Subject to any disclaimer, the term of this patent is extended or adjusted under 35 U.S.C. 154(b) by 464 days.

(21) Appl. No.: 15/452,518

(22) Filed: Mar. 7, 2017

(65) Prior Publication Data
US 2018/0256419 A1  Sep. 13, 2018

(51) Int. Cl.
| | | |
|---|---|---|
| A61F 13/56 | (2006.01) | |
| A61F 13/493 | (2006.01) | |
| A61F 13/494 | (2006.01) | |
| A61F 13/496 | (2006.01) | |
| A61F 13/53 | (2006.01) | |
| A61F 13/49 | (2006.01) | |

(52) U.S. Cl.
CPC ........ *A61F 13/5655* (2013.01); *A61F 13/493* (2013.01); *A61F 13/496* (2013.01); *A61F 13/4963* (2013.01); *A61F 13/49473* (2013.01); *A61F 13/53* (2013.01); *A61F 13/565* (2013.01); *A61F 2013/4948* (2013.01); *A61F 2013/49092* (2013.01)

(58) Field of Classification Search
CPC ................ A61F 13/493; A61F 13/5655; A61F 2013/49038
See application file for complete search history.

(56) References Cited

U.S. PATENT DOCUMENTS

| | | | | |
|---|---|---|---|---|
| 602,188 | A * | 4/1898 | Sittig | A41D 1/08 2/238 |
| 4,022,212 | A * | 5/1977 | Lovison | A61F 13/70 604/395 |
| 4,037,602 | A | 7/1977 | Hawthorne | |
| 4,446,575 | A * | 5/1984 | Davis | A41D 13/1254 2/400 |
| 4,619,649 | A | 10/1986 | Roberts | |
| 4,808,175 | A | 2/1989 | Hansen | |
| 4,930,161 | A * | 6/1990 | Cohen | A41D 13/1254 2/114 |
| 4,951,321 | A * | 8/1990 | Mortensen | A41B 9/001 2/405 |
| 5,207,662 | A | 5/1993 | James | |
| 5,797,824 | A | 8/1998 | Tracy | |
| 6,102,899 | A * | 8/2000 | Yimin | A61F 13/84 604/385.01 |
| 6,423,047 | B1 | 7/2002 | Webster | |
| 6,752,797 | B2 * | 6/2004 | Oba | A61F 13/42 604/395 |
| 7,993,322 | B2 * | 8/2011 | Brud | A61F 13/496 604/393 |
| 8,087,098 | B2 * | 1/2012 | Kimberly | A41B 9/001 2/227 |
| 8,518,007 | B2 | 8/2013 | Labit et al. | |
| 8,663,411 | B2 | 3/2014 | McCabe | |

(Continued)

*Primary Examiner* — Susan S Su
(74) *Attorney, Agent, or Firm* — Dergosits & Noah LLP

(57) ABSTRACT

A disposable diaper having a fully absorbent padded interior including a continuous liquid absorbent portion with no gaps or breaks in the absorbent padding along the sides of the diaper.

14 Claims, 20 Drawing Sheets

(56) References Cited

U.S. PATENT DOCUMENTS

| | | | |
|---|---|---|---|
| 2002/0138065 A1* | 9/2002 | Yeater | A61F 13/49011 |
| | | | 604/395 |
| 2003/0149418 A1 | 8/2003 | Katz | |
| 2006/0069376 A1* | 3/2006 | Miller | A61F 13/49001 |
| | | | 604/385.201 |
| 2006/0271009 A1 | 11/2006 | Cartier et al. | |
| 2009/0036857 A1 | 2/2009 | Sherrod | |
| 2014/0243775 A1* | 8/2014 | Buell | A61F 13/496 |
| | | | 604/385.16 |
| 2016/0095764 A1 | 4/2016 | Seitz et al. | |
| 2018/0036183 A1* | 2/2018 | Espinosa De Los Monteros | A61F 13/15203 |

* cited by examiner

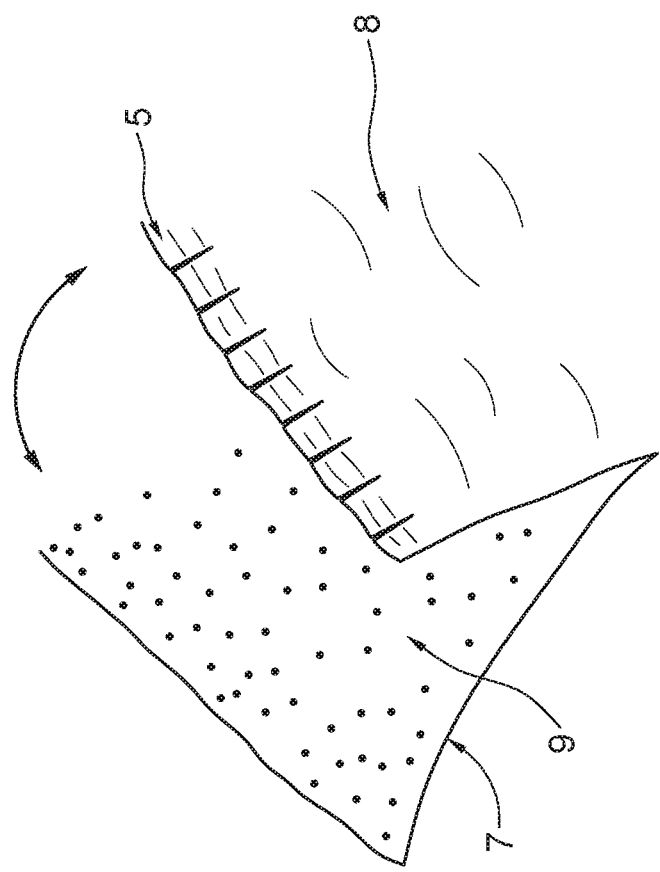

FULLY PADDED DISPOSABLE DIAPER

TECHNICAL FIELD

The present disclosure relates to fully padded disposable diapers particularly suitable for toddler boys.

BACKGROUND

Disposable diapers for boys and girls have become very common, and have almost entirely replaced the old fashioned cloth diapers. Disposable diapers are available in a number of sizes to be worn by infant boys and girls, and by older children who are not yet fully toilet trained.

Most conventional disposable diapers follow the design of older cloth diapers. The diapers are generally rectangular in shape and include a front section and a back section being connected through a middle (crotch) section, and further include two rounded cutouts positioned in approximately the middle area of the diaper. The new diaper is opened flat, and the baby is laid on the back panel with his or her legs positioned in the cut outs.

Fastening means, such as for example VELCRO® brand hook and loop fasteners, or adhesive strips, are provided on the sides and front side of the diaper to secure the diaper around the baby's waist. Elastic bands around the waist and leg openings may be provided to ensure a better fit for the diaper.

A more modern diaper design is the pull-up diaper, where the back panel and front panel are connected with a side seam or side panel, and leg openings and the torso opening are elasticized without absorbing padding.

Most disposable diapers comprise an inner layer, an outer layer, and an absorbent padding positioned between the inner and the outer layers. The inner layer is situated next to baby's skin and provides a comfortable cushion between the baby and the absorbent core. The absorbent padding absorbs the liquids, and the outer layer protects the baby's clothing from moisture.

Conventional diapers do not have absorbent padding covering the fastening means or seams, since providing absorbent padding on the fasteners or seam will prevent the closing of the diaper, or opening of the seam (e.g., to remove due to a messy accident). Conventional diapers also do not have absorbent materials extending all the way to the elastic portions around the waist and leg openings.

During sleep, toddler boys become more likely to urinate up or sideways. Conventional diapers do not provide an adequate protection against leakage and seepage at the location of the fasteners or seams along the sides of the diaper or in the area of the elastic bands at the waist and leg openings. What is needed in the art is a fully padded diaper with a seam located on the back of the diaper, having the padded material extending all the way up to the elastic portions around the top of the diaper and to the elastic portions surrounding the leg holes, in order to provide excellent moisture and leakage protection for toddler boys where it is needed the most—around the sides and the waistband and leg openings.

SUMMARY

Accordingly, it is an objective of the instant disclosure to teach a sleep-time diaper having a fully absorbent padded interior with no gaps or breaks in the absorbent padding along the sides of the diaper due to the presence of seams or fasteners along the sides of the diaper, with the absorbent padding extending to the bottom edge of the top elastic stretch portion of the diaper, to the outer edge of the elastic material surrounding the leg holes, and to the outer edges of the seam on the back of the diaper. In this embodiment, the absorbent material does not cover the top elastic stretch portion of the diaper, does not cover the elastic material surrounding the leg holes, and does not cover the seam on the back of the diaper.

It is another objective of the instant disclosure to teach a sleep-time diaper having a fully absorbent padded interior with no gaps or breaks in the absorbent padding along the sides of the diaper due to the presence of seams or fasteners along the sides of the diaper, with the absorbent padding covering the top elastic stretch portion of the diaper and the seam on the back of the diaper and extending to the outer edge of the elastic material surrounding the leg holes. In this embodiment, the absorbent material does not cover the elastic material surrounding the leg holes.

It is another objective of the instant disclosure to teach a sleep-time diaper having a fully absorbent padded interior with no gaps or breaks in the absorbent padding along the sides of the diaper due to the presence of seams or fasteners along the sides of the diaper, with the absorbent padding covering the elastic material surrounding the leg holes. In this embodiment, the absorbent material does not cover the top elastic stretch portion of the diaper and does not cover the seam on the back of the diaper.

It is another objective of the instant disclosure to teach a sleep-time diaper having a fully absorbent padded interior with no gaps or breaks in the absorbent padding along the sides of the diaper due to the presence of seams or fasteners along the sides of the diaper, with the absorbent padding covering the top elastic stretch portion of the diaper, covering the seam on the back of the diaper, and covering the elastic material surrounding the leg holes.

BRIEF DESCRIPTION OF THE DRAWINGS

FIG. 20 is a view of a enlarged portion of the disposable diaper of FIG. 16 with the interior surface material partially peeled back to expose the absorbent padded lining.

DETAILED DESCRIPTION

Figure 1:
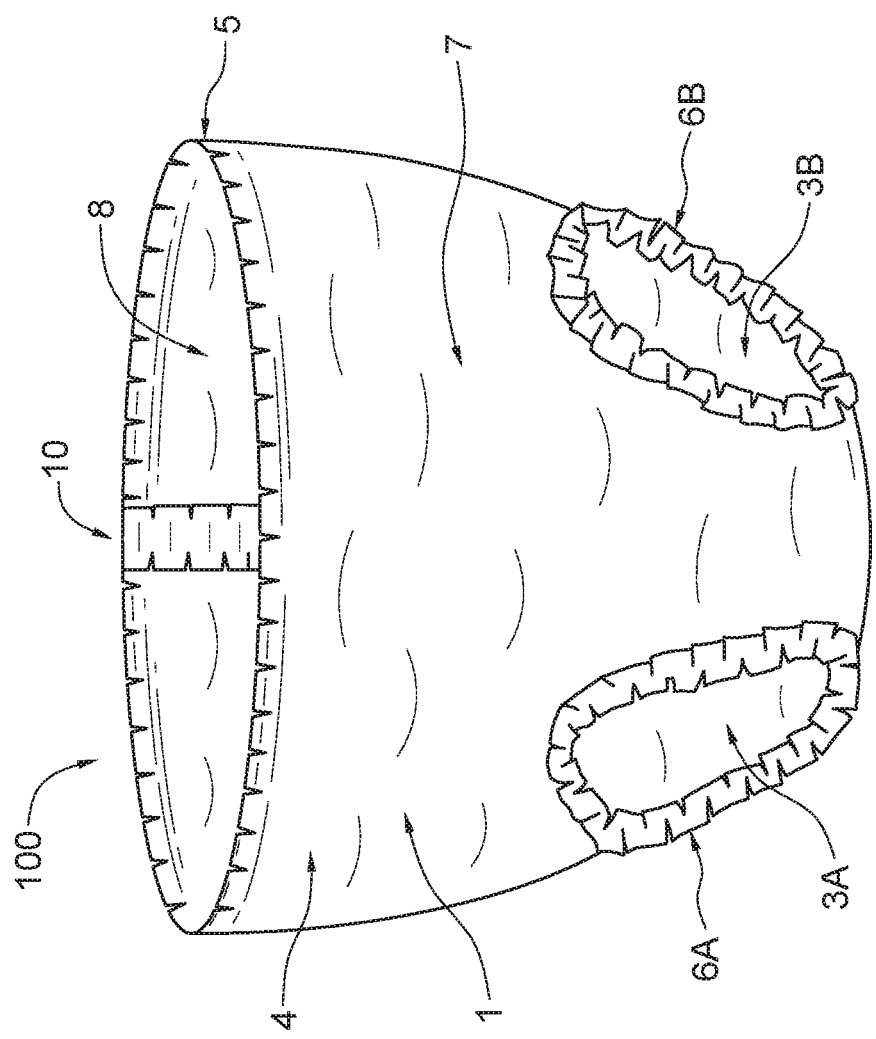
FIG. 1 is a perspective view of the front of the disposable diaper according to the first embodiment of the invention.
Figure 2:
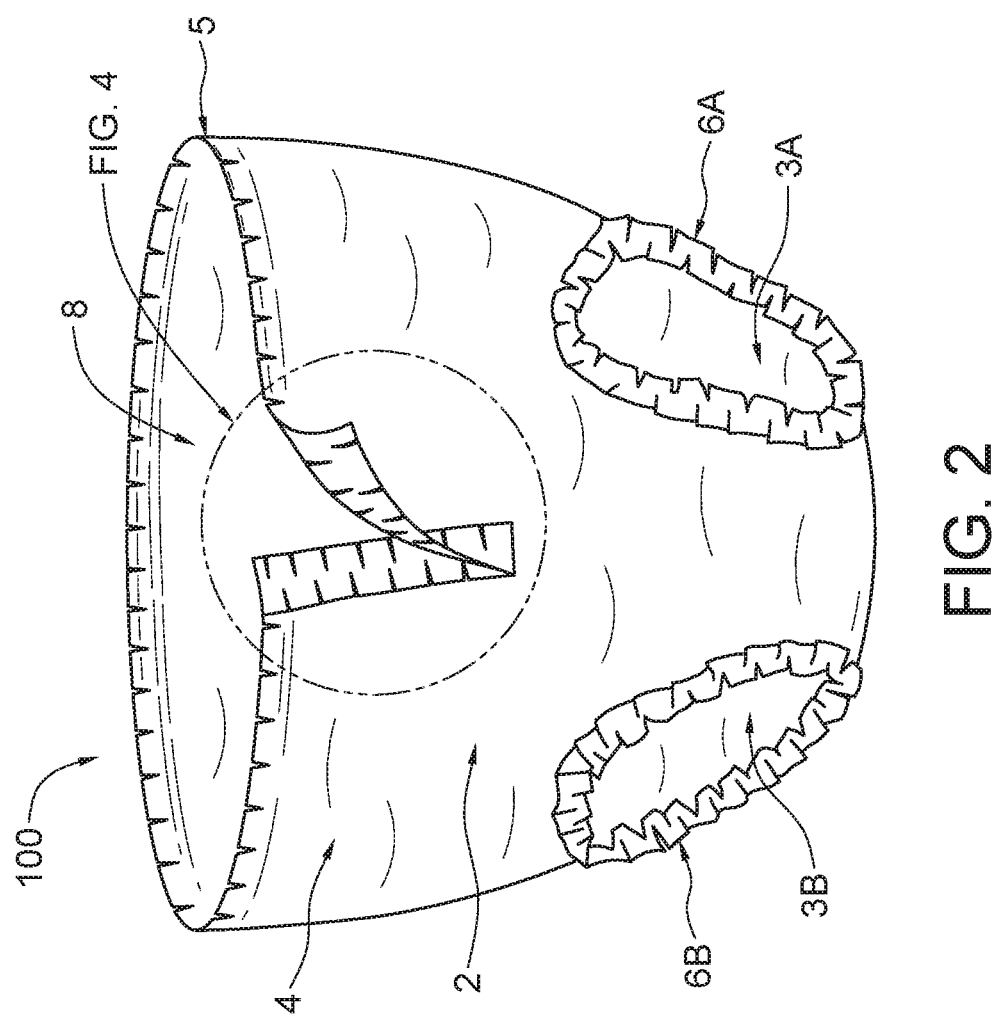
FIG. 2 is a perspective view of the back of the disposable diaper according to the first embodiment of the invention.

A fully padded sleep-time disposable diaper according to embodiments of the present disclosure will now be described with reference to FIGS. 1-20. Persons of ordinary skill in the art would understand that various changes can be made to the preferred embodiments described herein without departing from the spirit of the disclosure.

FIGS. 1-5 illustrate a fully padded disposal diaper 100 according to the first embodiment of the invention, which is shaped to fit a small body (not shown) just like briefs (underwear) and may be constructed of conventional materials. Diaper 100 comprises an impermeable exterior surface material 7, a permeable interior surface material 8 and an absorbent padded lining 9. Exterior surface material 7 is preferably made from a fabric that is water and fluid resistant in order to protect the toddlers' outer garments from moisture, such as for example a nonwoven or breathable polyethylene film. Interior surface material 8 is preferably made from nonwoven fabrics, such as for example GMO free wheat, corn, bamboo, cotton, pulp, or synthetic polymers, to provide a soft lining for increased comfort of the toddler wearing the diaper.

Diaper 100 includes a front portion 1, a back portion 2, leg holes 3a and 3b, and a top portion 4 that includes an elastic stretch portion 5 and a seam 10, described below. The front portion 1 and the back portion 2 are formed as a single continuous body structure, just like underwear briefs, with elasticized leg openings and elasticized torso opening. Elastic stretch portion 5 allows the diaper to easily accommodate children of different sizes and girths. Leg holes 3a and 3b are defined by stretch leg portions 6a and 6b comprising one or more elastic threads sewn into the diaper. Stretch leg portions 6a and 6b allow the leg holes to stretch in order to accommodate legs of various sizes.

Figure 5:
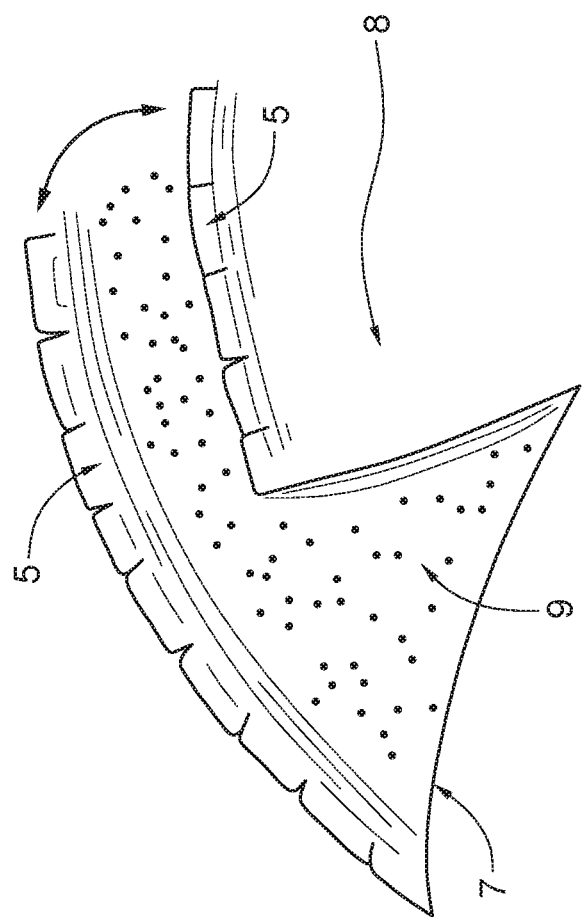
FIG. 5 is a view of a enlarged portion of the disposable diaper of FIG. 1 with the interior surface material partially peeled back to expose the absorbent padded lining.
Figure 6:
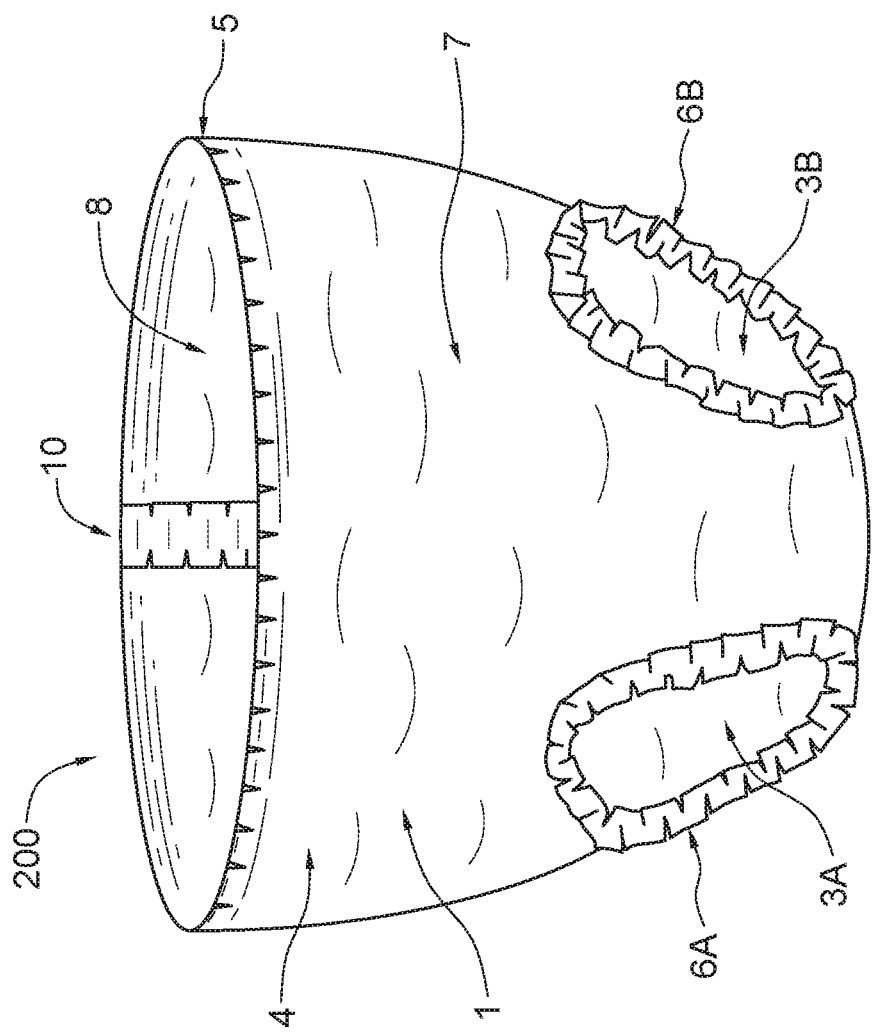
FIG. 6 is a perspective view of the front of the disposable diaper according to the second embodiment of the invention.
Figure 7:
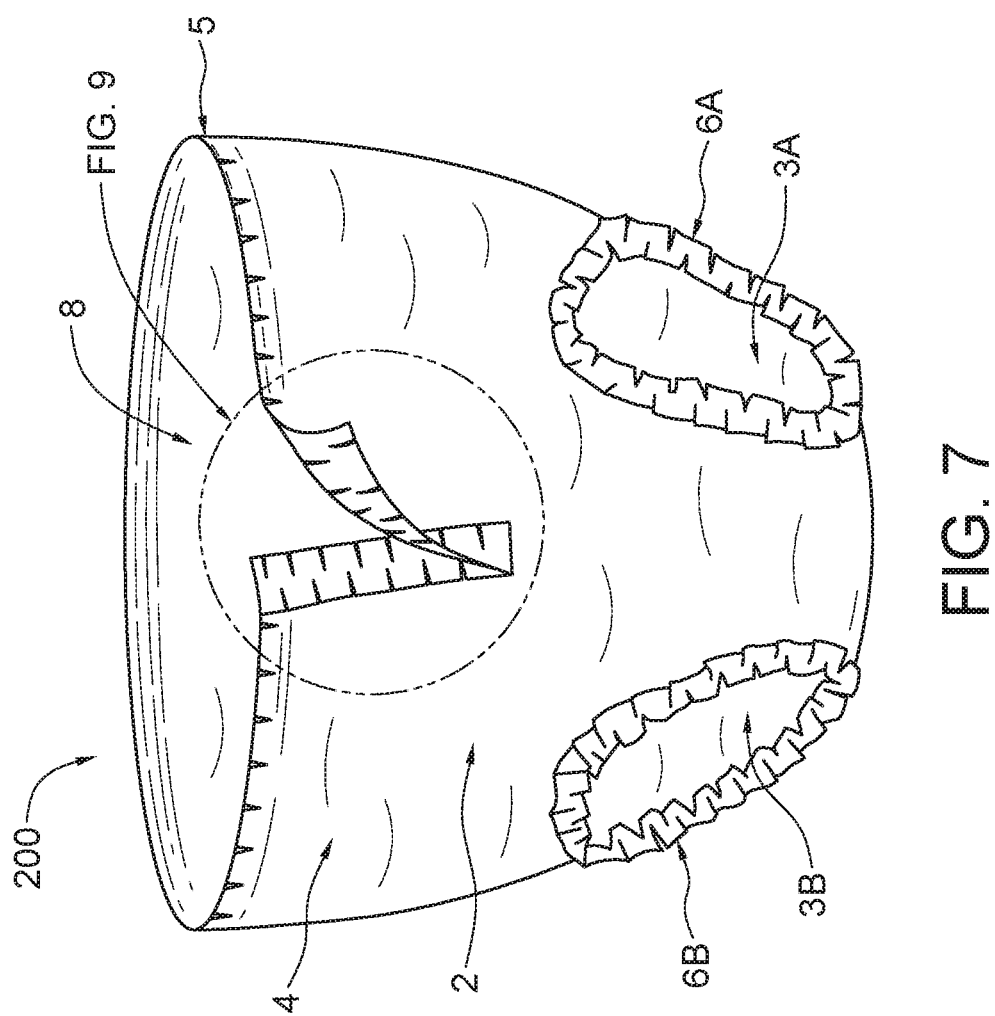
FIG. 7 is a perspective view of the back of the disposable diaper according to the second embodiment of the invention.

One or more layers of absorbent padded lining 9, such as eco friendly, chlorine and fragrance free, sustainable hypoallergenic, naturally breathable liquid absorbing materials formed as usable fabrics, for example, GMO free wheat, corn, bamboo, cotton, pulp, or synthetic polymers, are situated between exterior surface material 7 and interior surface material 8 (FIG. 5).

Exterior surface material 7, layers of absorbent padded lining 9, and interior surface material 8 may be affixed to one another by stitching, by a suitable adhesive, or by other conventional means known in the art. For example, stitching may be done at the torso opening and leg openings to secure an elastic material with the interior surface material 7, the absorbent lining 9, and the exterior surface material 8.

Figure 4:
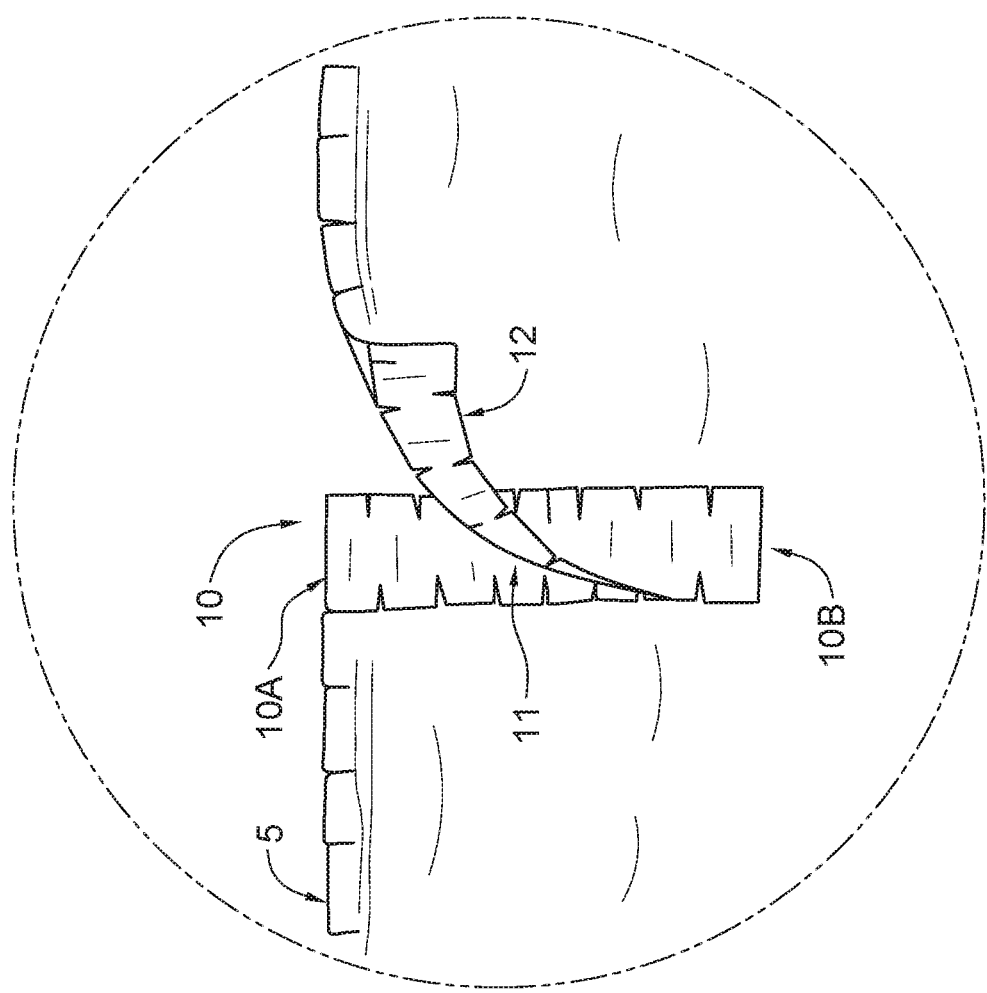
FIG. 4 is a portion of FIG. 2 enlarged to show the partially separable seam of the disposable diaper.

As illustrated in FIG. 4, back portion 2 of diaper 100 includes a partially separable seam 10 extending downward from the torso opening. Seam 10 comprises two overlapping areas 11 and 12 which may be secured to each other by including VELCRO® brand hook fasteners on overlapping area 11, and including VELCRO® brand loop fasteners on overlapping area 12, or vice versa. Other conventional ways of securing overlapping areas 11 and 12 to close seam 10 may be used including non toxic adhesive at seams and joints. In a preferred embodiment, seam 10 is approximately 4 inches long as measured from point 10a at the torso opening to point 10b on the body portion. Locating seam 10 on the back side of the diaper, as opposed to locating the seam on a side of the diaper, and having a partially separable seam that reaches down a portion of the back of the diaper, as opposed to having a fully separable seam going all the way down the side of the diaper so that the diaper is fully openable along the seam, is particularly advantageous for toddler boys, because at that age, boys tend urinate up or sideways, and having no seams or fastening means on the sides ensures the greatest protection from moisture and leakage at the sides of the diaper.

Figure 3:
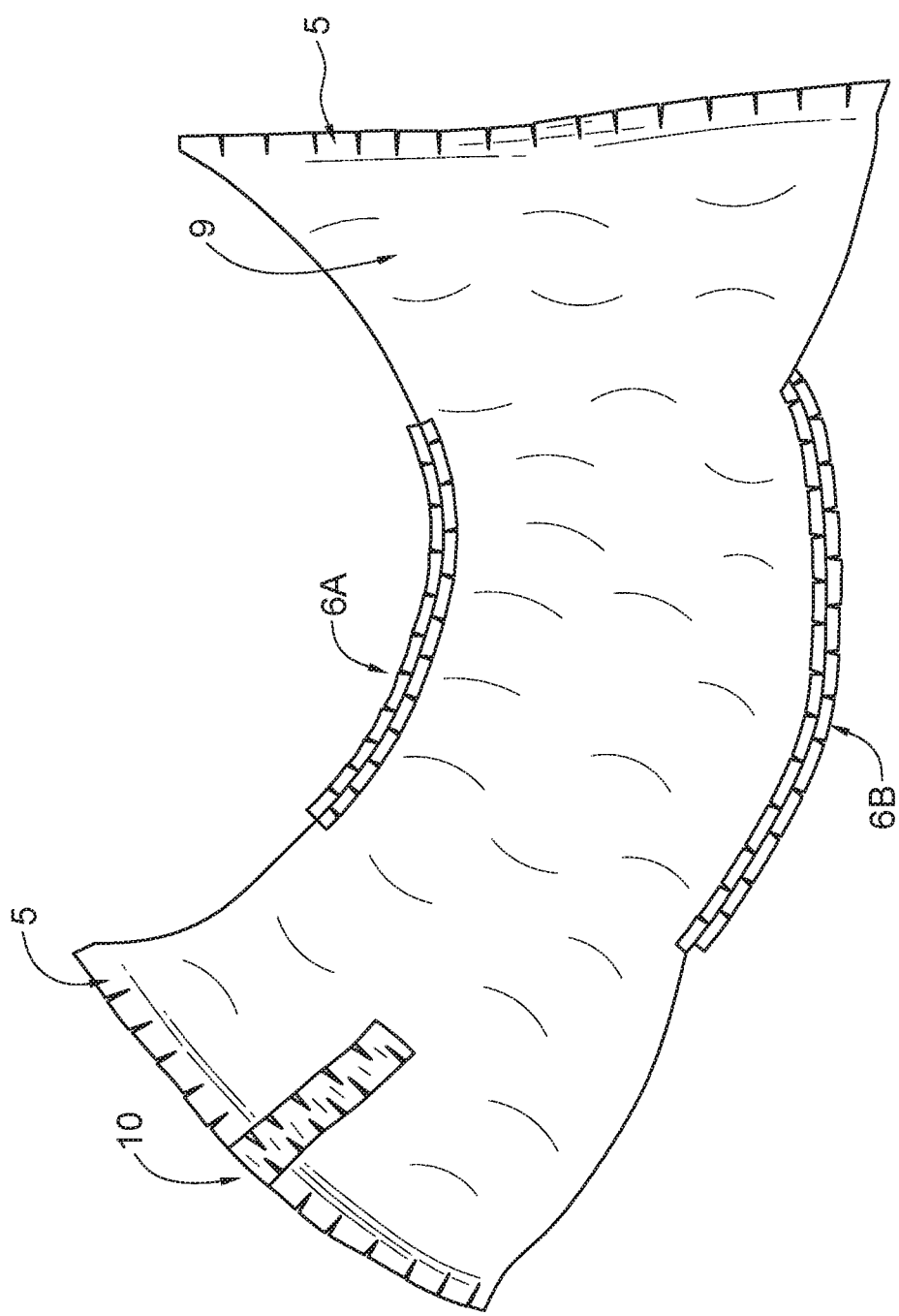
FIG. 3 is a laid-open view of the disposable diaper of FIG. 1 split at the sides and having the interior surface material removed to expose the absorbent padded lining.

Interior of diaper 100 includes absorbent padded lining 9 disposed between exterior surface material 7 and interior surface material 8. FIG. 5 is a view of an enlarged portion of the disposable diaper of FIG. 1 with the interior surface material 7 partially peeled back to expose the absorbent padded lining. FIG. 5 illustrates absorbent padded lining 9 situated between exterior surface material 7 and interior surface material 8. FIG. 3, which is a laid-open view of the disposable diaper of FIG. 1 split at the sides with the interior surface material 7 removed to expose the absorbent padded lining, illustrates absorbent lining 9 in the interior of the disposable diaper according to the first embodiment of the invention. Absorbent padded lining 9 extends to the bottom edge of elastic stretch top portion 5, around the edges of seam 10, and to the interior edge of the stretch leg portions 6a and 6b. In this embodiment, absorbent padded lining 9 does not extend to the top edge of the elastic stretch portion 5 of the diaper and does not extend into the stretch leg portions 6a and 6b of the diaper.

Providing absorbent padded lining 9 over the entire area of interior portion material 8, including all the way to the bottom edge of the elastic stretch top portion 5 and to the interior edges of the elastic portions 6a and 6b of leg holes 3a and 3b, is particularly advantageous for toddler boys because it provides better protection from moisture and leakage than conventional diapers with side seams or fasteners.

Figure 8:
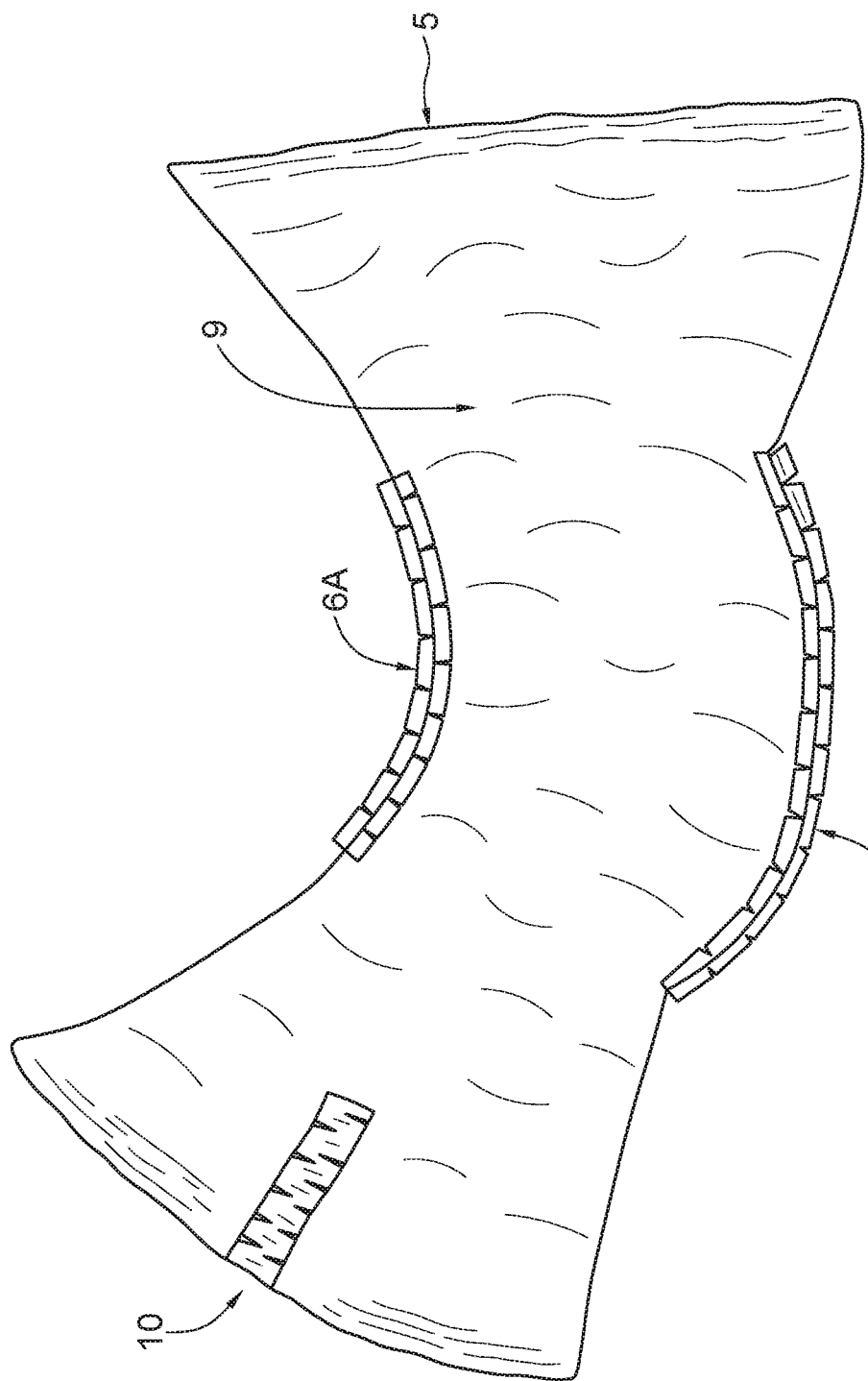
FIG. 8 is a laid-open view of the disposable diaper of FIG. 6 split at the sides and having the having the interior surface material removed to expose the absorbent padded lining.
Figure 9:
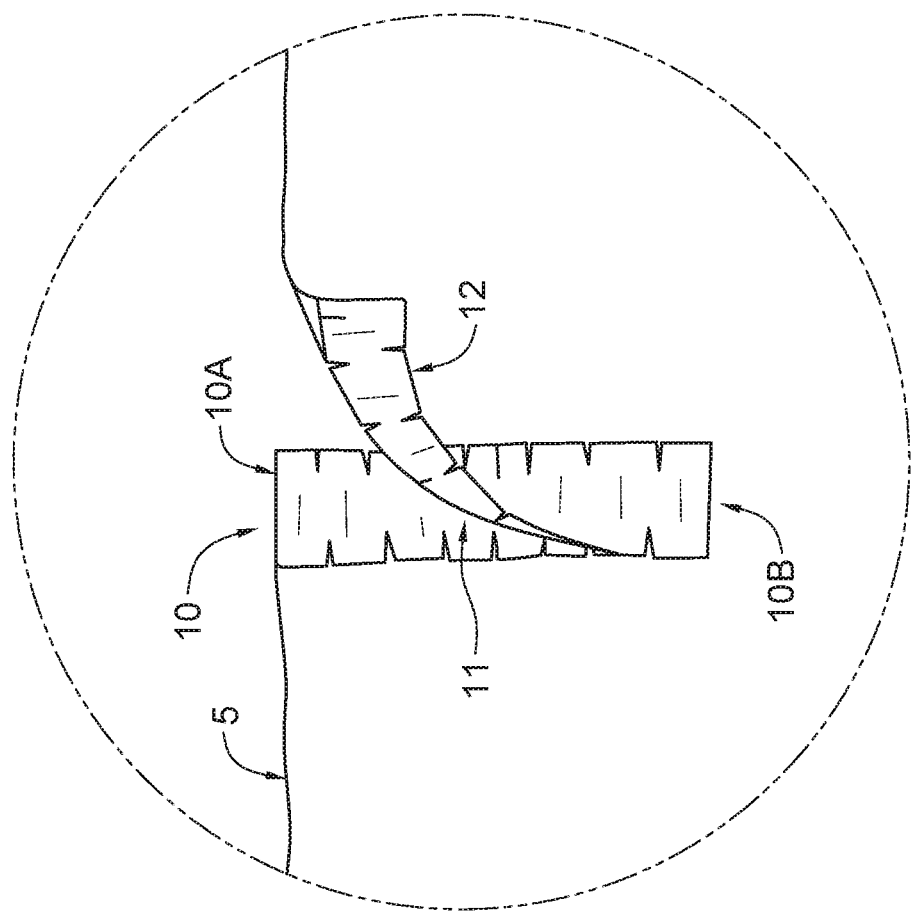
FIG. 9 is a portion of FIG. 7 enlarged to show the partially separable seam of the disposable diaper.
Figure 10:
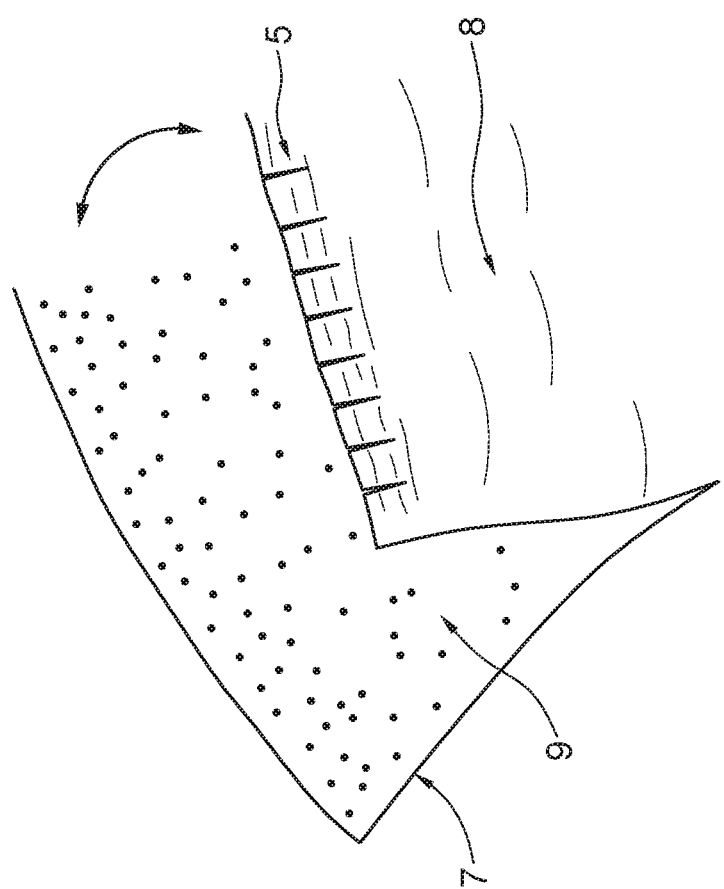
FIG. 10 is a view of a enlarged portion of the disposable diaper of FIG. 6 with the interior surface material partially peeled back to expose the absorbent padded lining.
Figure 11:
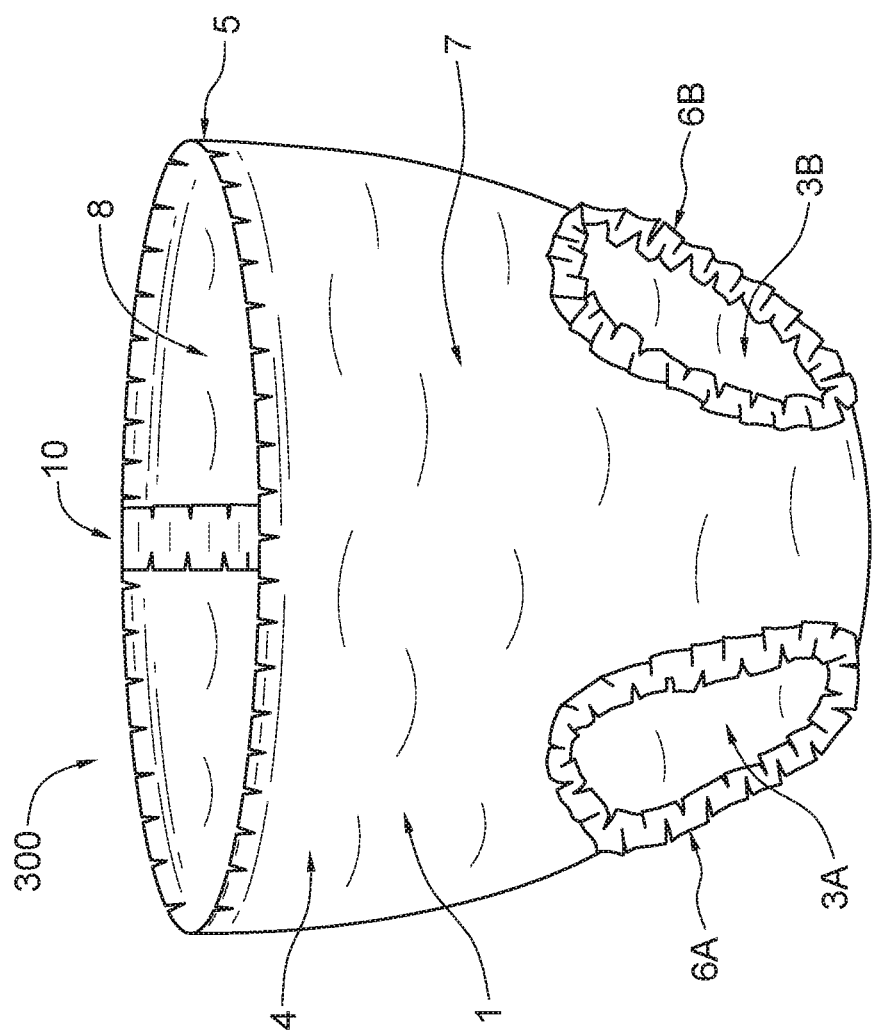
FIG. 11 is a perspective view of the front of the disposable diaper according to the third embodiment of the invention.
Figure 12:
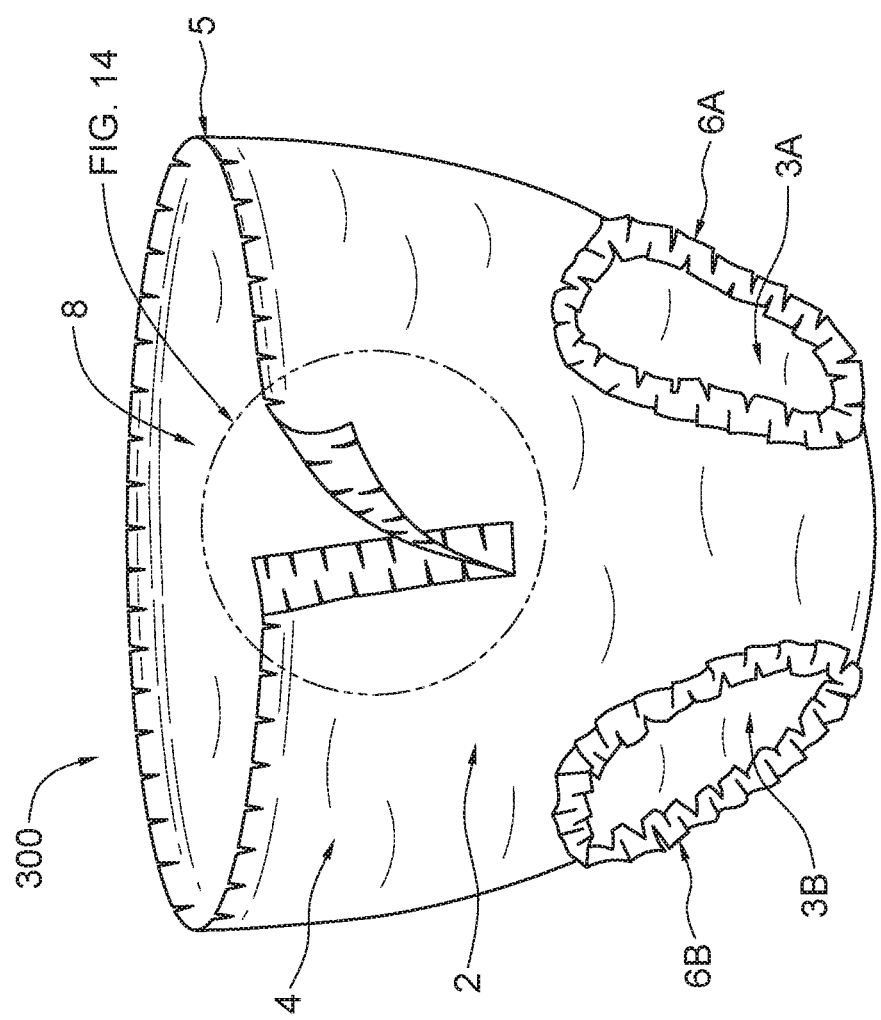
FIG. 12 is a perspective view of the back of the disposable diaper according to the third embodiment of the invention.

FIGS. 6-10 illustrate a fully padded disposal diaper 200 according to the second embodiment of the invention. Diaper 200 includes a front portion 1, a back portion 2, leg holes 3a and 3b, and a top portion 4 that includes an elastic stretch portion 5 and a seam 10. One or more layers of absorbent padded lining 9, such as eco friendly, chlorine and fragrance free, sustainable hypoallergenic, naturally breathable liquid absorbing materials formed as usable fabrics, for example, GMO free wheat, corn, bamboo, cotton, pulp, or synthetic polymers, are placed between exterior surface material 7 and interior surface material 8 (FIG. 10).

As illustrated in FIG. 9, back portion 2 of diaper 200 includes a partially separable seam 10 extending downward from the torso opening. Seam 10 comprises two overlapping areas 11 and 12 which may be secured to each other by including VELCRO® brand hook fasteners on overlapping area 11, and including VELCRO® brand loop fasteners on overlapping area 12, or vice versa. In a preferred embodiment, seam 10 is approximately 4 inches long as measured from point 10a at the torso opening to point 10b on the body portion.

Interior of diaper 200 includes absorbent padded lining 9 disposed between exterior surface material 7 and interior surface material 8. FIG. 10 is a view of an enlarged portion of the disposable diaper of FIG. 6 with the interior surface material 7 partially peeled back to expose the absorbent padded lining. FIG. 10 illustrates absorbent padded lining 9 situated between exterior surface material 7 and interior surface material 8. FIG. 8, which is a laid-open view of the disposable diaper of FIG. 6 split at the sides with the interior surface material 7 removed to expose the absorbent padded lining, illustrates absorbent lining 9 in the interior of the disposable diaper according to the second embodiment of the invention. Absorbent padded lining 9 extends to the top edge of elastic stretch top portion 5, around the edges of seam 10, and to the interior edge of the stretch leg portions 6a and 6b. In this embodiment, absorbent padded lining 9 does not extend into the stretch leg portions 6a and 6b of the diaper.

Figure 13:
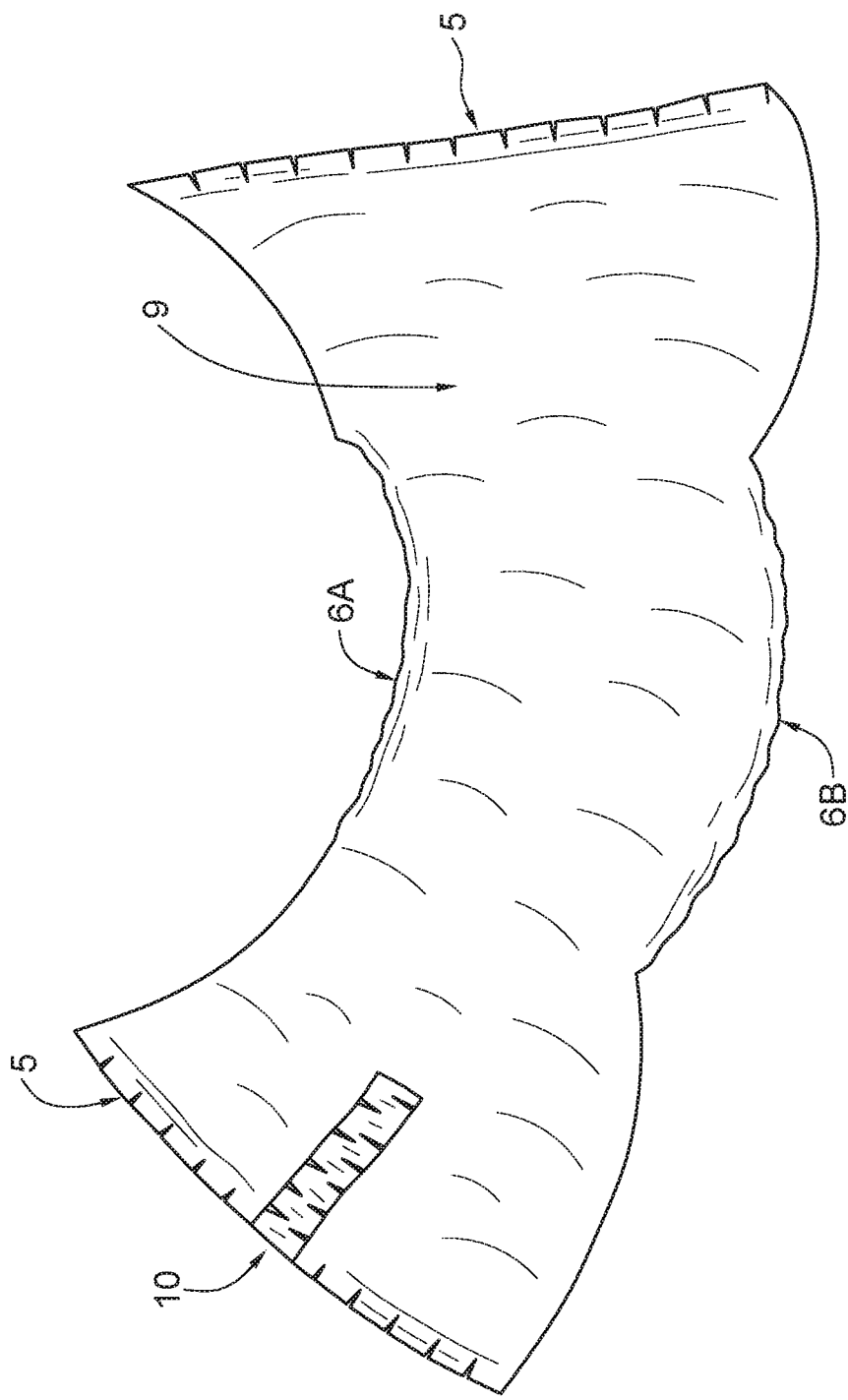
FIG. 13 is a laid-open view of the disposable diaper of FIG. 11 split at the sides and having the having the interior surface material removed to expose the absorbent padded lining.
Figure 14:
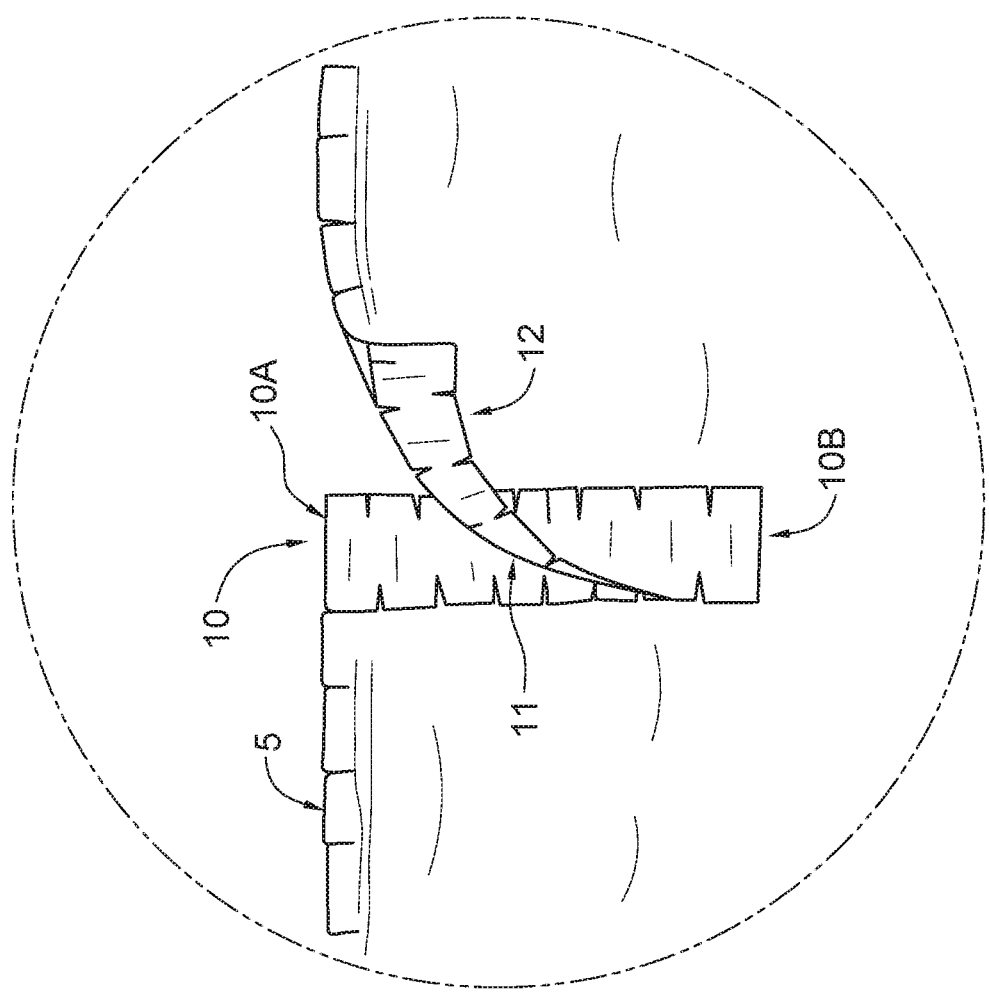
FIG. 14 is a portion of FIG. 12 enlarged to show the partially separable seam of the disposable diaper.
Figure 15:
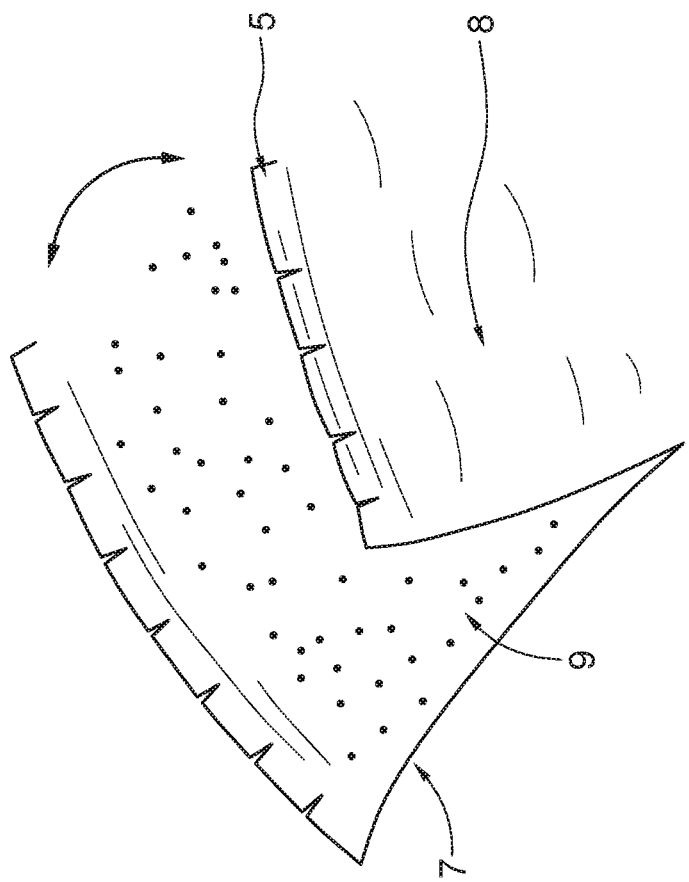
FIG. 15 is a view of a enlarged portion of the disposable diaper of FIG. 11 with the interior surface material partially peeled back to expose the absorbent padded lining.
Figure 16:
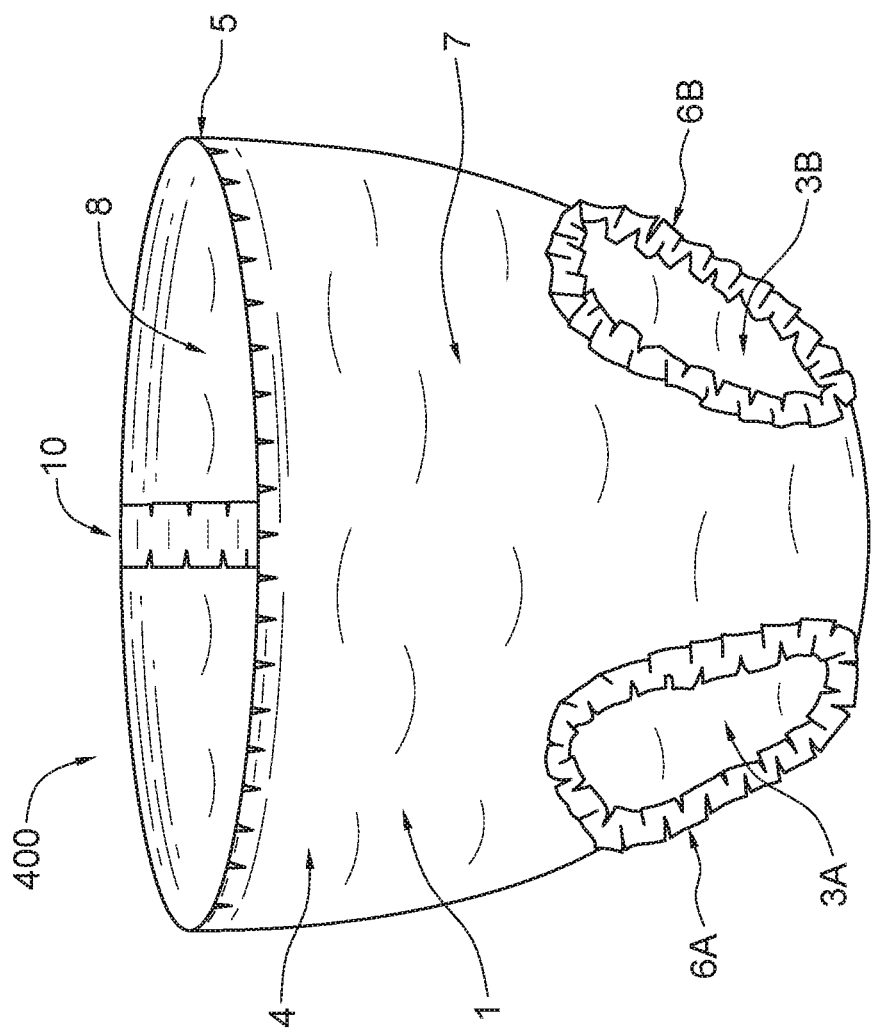
FIG. 16 is a perspective view of the front of the disposable diaper according to the fourth embodiment of the invention.
Figure 17:
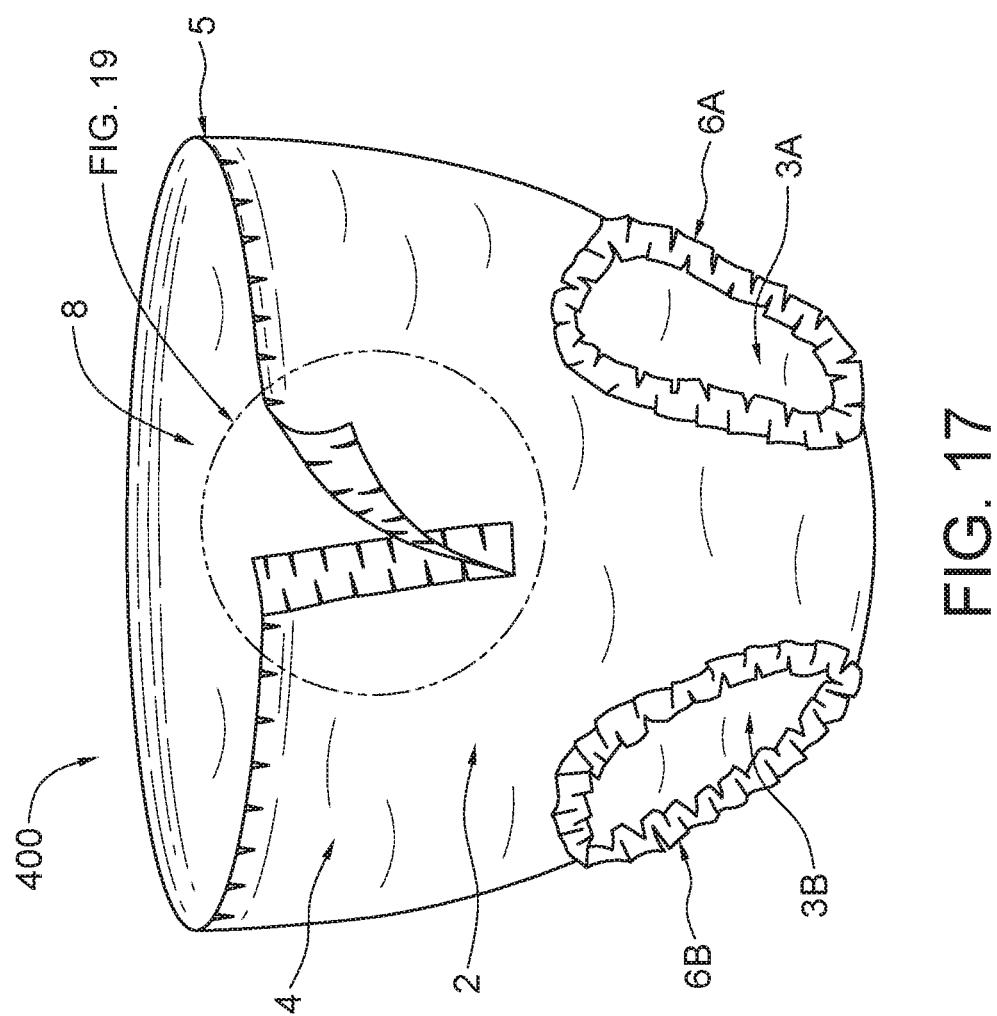
FIG. 17 is a perspective view of the back of the disposable diaper according to the fourth embodiment of the invention.

FIGS. 11-15 illustrate a fully padded disposal diaper 300 according to the third embodiment of the invention. Diaper 300 includes a front portion 1, a back portion 2, leg holes 3a and 3b, and a top portion 4 that includes an elastic stretch portion 5 and a seam 10. One or more layers of absorbent padded lining 9, such as eco friendly, chlorine and fragrance free, sustainable hypoallergenic, naturally breathable liquid absorbing materials formed as usable fabrics, for example, GMO free wheat, corn, bamboo, cotton, pulp, or synthetic polymers, are placed between exterior surface material 7 and interior surface material 8 (FIG. 15).

As illustrated in FIG. 14, back portion 2 of diaper 300 includes a partially separable seam 10 extending downward from the torso opening. Seam 10 comprises two overlapping areas 11 and 12 which may be secured to each other by including VELCRO® brand hook fasteners on overlapping area 11, and including VELCRO® brand loop fasteners on overlapping area 12, or vice versa. In a preferred embodiment, seam 10 is approximately 4 inches long as measured from point 10a at the torso opening to point 10b on the body portion.

Interior of diaper 300 includes absorbent padded lining 9 disposed between exterior surface material 7 and interior surface material 8. FIG. 15 is a view of an enlarged portion of the disposable diaper of FIG. 11 with the interior surface material 7 partially peeled back to expose the absorbent padded lining. FIG. 15 illustrates absorbent padded lining 9 situated between exterior surface material 7 and interior surface material 8. FIG. 13, which is a laid-open view of the disposable diaper of FIG. 11 split at the sides with the interior surface material 7 removed to expose the absorbent padded lining, illustrates absorbent lining 9 in the interior of the disposable diaper according to the third embodiment of the invention. Absorbent padded lining 9 extends to the bottom edge of elastic stretch top portion 5, around the edges of seam 10, and extends into the stretch leg portions 6a and 6b. In this embodiment, absorbent padded lining 9 does not extend to the top edge of the elastic stretch portion 5 of the diaper.

FIGS. 16-20 illustrate a fully padded disposal diaper 400 according to the fourth embodiment of the invention. Diaper 400 includes a front portion 1, a back portion 2, leg holes 3a and 3b, and a top portion 4 that includes an elastic stretch portion 5 and a seam 10. One or more layers of absorbent padded lining 9, such as eco friendly, chlorine and fragrance free, sustainable hypoallergenic, naturally breathable liquid absorbing materials formed as usable fabrics, for example, GMO free wheat, corn, bamboo, cotton, pulp, or synthetic polymers, are placed between exterior surface material 7 and interior surface material 8 (FIG. 20).

Figure 19:
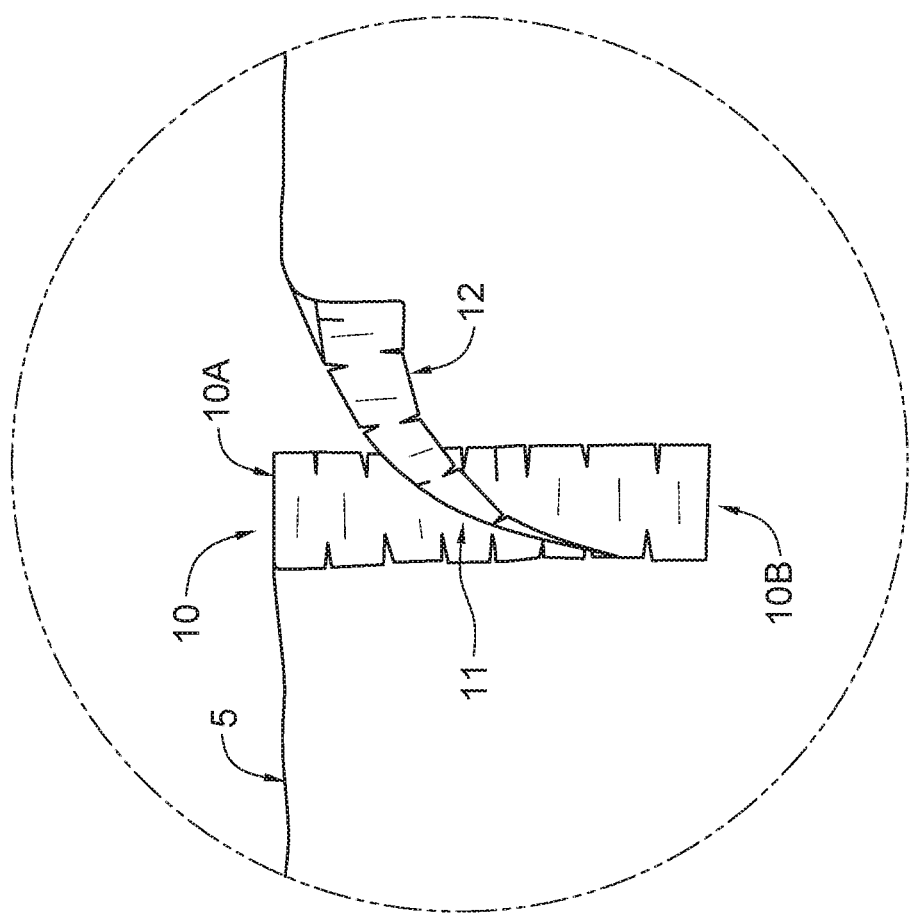
FIG. 19 is a portion of FIG. 17 enlarged to show the partially separable seam of the disposable diaper.

As illustrated in FIG. 19, back portion 2 of diaper 400 includes a partially separable seam 10 extending downward from the torso opening. Seam 10 comprises two overlapping areas 11 and 12 which may be secured to each other by including VELCRO® brand hook fasteners on overlapping area 11, and including VELCRO® brand loop fasteners on overlapping area 12, or vice versa. In a preferred embodiment, seam 10 is approximately 4 inches long as measured from point 10a at the torso opening to point 10b on the body portion.

Figure 18:
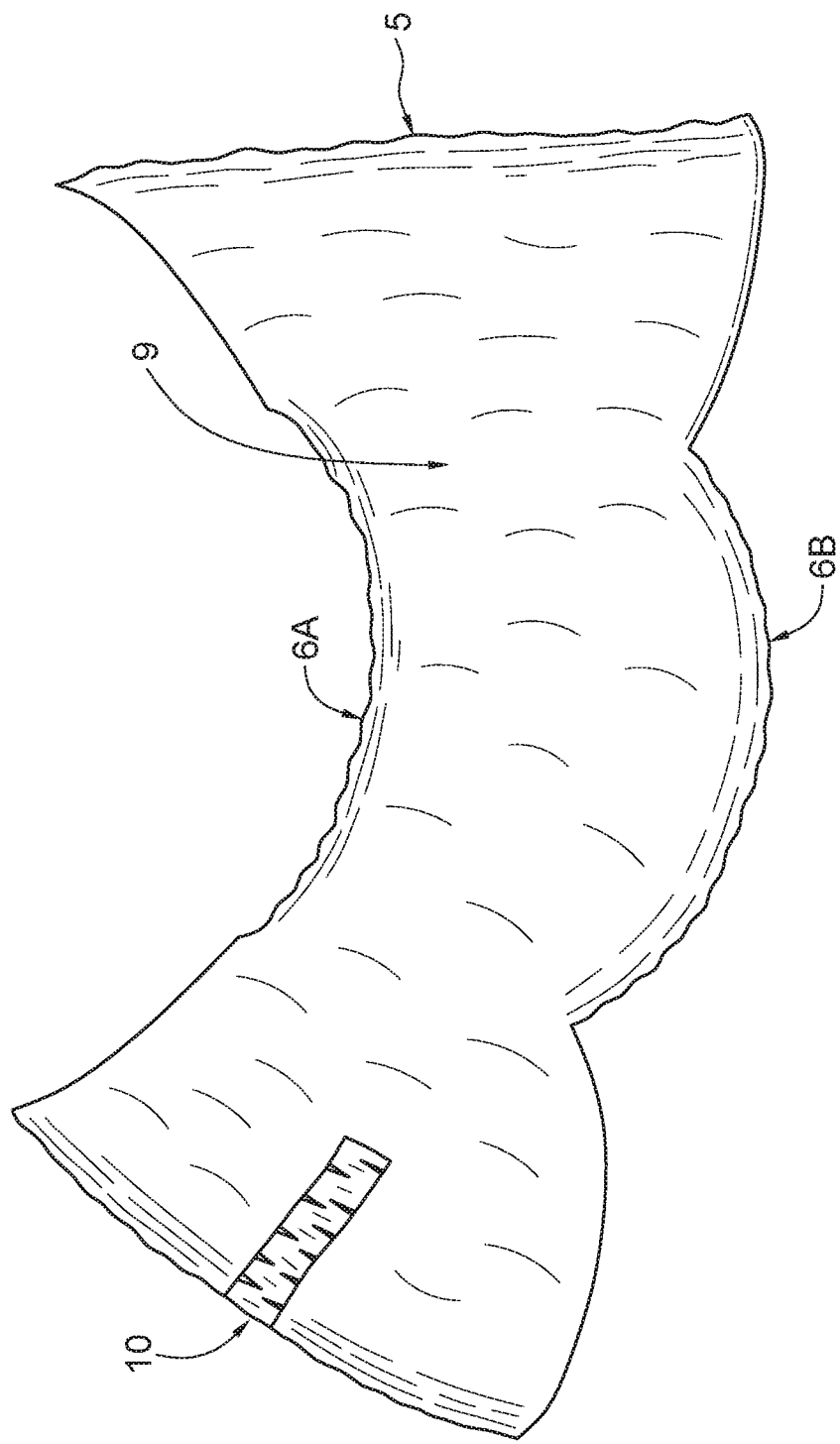
FIG. 18 is a laid-open view of the disposable diaper of FIG. 16 split at the sides and having the having the interior surface material removed to expose the absorbent padded lining.

Interior of diaper 400 includes absorbent padded lining 9 disposed between exterior surface material 7 and interior surface material 8. FIG. 20 is a view of an enlarged portion of the disposable diaper of FIG. 16 with the interior surface material 7 partially peeled back to expose the absorbent padded lining. FIG. 20 illustrates absorbent padded lining 9 situated between exterior surface material 7 and interior surface material 8. FIG. 18, which is a laid-open view of the disposable diaper of FIG. 16 split at the sides with the interior surface material 7 removed to expose the absorbent padded lining, illustrates absorbent lining 9 in the interior of the disposable diaper according to the fourth embodiment of the invention. Absorbent padded lining 9 extends to the top edge of elastic stretch top portion 5, around the edges of seam 10, and extends into the stretch leg portions 6a and 6b

The above mentioned is only exemplary embodiments of the present invention. It should be noted, for persons of ordinary skill in this art field, improvements and modifications within the spirit of the present invention can be further made, and such improvements and modifications should be seemed to be included in the claimed scope of the present invention.

What is claimed is:

1. A disposable sleep-time diaper comprising:
   a body portion having a front and a rear;
   two leg holes surrounded by elastic stretch portions;
   an elastic stretch portion at the top of the body portion;
   a continuous liquid-impermeable exterior portion;
   a continuous liquid-permeable interior portion;
   a continuous liquid absorbent portion disposed between the liquid-impermeable exterior portion and the liquid-permeable interior portion;
   a seam provided in the rear portion of the body and extending along a segment of the rear portion of the body;
   a fastener operable to close and open the seam,
   wherein the continuous liquid absorbent portion overlaps the fastener in a thickness direction of the diaper.

2. A disposable sleep-time diaper according to claim 1, wherein the continuous liquid absorbent portion extends to a bottom edge of the elastic stretch portion at the top of the body portion of the diaper.

3. A disposable sleep-time diaper according to claim 1, wherein the continuous liquid absorbent portion extends into the elastic stretch portion at the top of the body portion of the diaper.

4. A disposable sleep-time diaper according to claim 1, wherein the elastic stretch portions at the leg holes having an outer edge that defines the leg hole and an inner edge that is inbound of the outer edge such that a distance between the outer and inner edges define a width of the elastic stretch portions all around the circumference of the leg holes, and the continuous liquid absorbent portion extends to the inner edge of the elastic stretch portions at the leg holes.

5. A disposable sleep-time diaper according to claim 1, wherein the continuous liquid absorbent portion extends into the elastic stretch portions surrounding the leg holes.

6. A disposable sleep-time diaper according to claim 1, wherein the continuous liquid absorbent portion extends into the elastic stretch portion at the top of the body portion of the diaper and extends into the elastic stretch portions surrounding the leg holes.

7. A disposable sleep-time diaper according to claim 1, wherein the fastener comprises two overlapping portions releasably connected to each other.

8. A disposable sleep-time diaper according to claim 1, wherein the fastener is four inches long.

9. The disposable diaper of claim 1 further comprising a torso opening and the leg holes having an elasticized finish.

10. A disposable diaper having a body with a brief-like shape with first and second leg openings and a torso opening, comprising:

the body having a liquid absorbent middle layer affixed between a liquid impermeable exterior layer and a liquid permeable inner layer;

an open seam provided in a rear portion of the body and extending downward from the torso opening; and a fastener affixed at the seam and operable to close and open the seam, wherein the liquid impermeable exterior layer, the liquid absorbent middle layer, and the liquid impermeable exterior layer are affixed to each other at the torso opening and the leg openings.

11. The disposable diaper of claim 10, the seam further comprising a pair of overlapping body portions.

12. The disposable diaper of claim 10, the fastener comprising a hook and loop fastener disposed on respective overlapping body portions.

13. The disposable diaper of claim 10, wherein the liquid impermeable exterior layer, the liquid absorbent middle layer, and the liquid impermeable exterior layer are stitched together at the torso opening and the leg openings.

14. The disposable diaper of claim 10, further comprising the torso opening and the leg openings having an elasticized finish.

\* \* \* \* \*